United States Patent [19]

Buzby et al.

[11] Patent Number: 4,956,280
[45] Date of Patent: Sep. 11, 1990

[54] BIPHASIC SHUTTLE VECTORS

[75] Inventors: Jeffrey S. Buzby, Los Angeles, Calif.; Ronald D. Porter; S. Edward Stevens, Jr., both of State College, Pa.

[73] Assignee: Research Corporation, New York, N.Y.

[21] Appl. No.: 927,772

[22] Filed: Nov. 6, 1986

[51] Int. Cl.$^5$ .................. C12P 21/00; C12P 19/34; C12P 1/04; C12N 15/00; C07H 15/12

[52] U.S. Cl. ................... 435/69.1; 435/91; 435/170; 435/172.3; 435/252.3; 435/320; 435/822; 435/252.1; 536/27; 935/6; 935/22; 935/60; 935/72

[58] Field of Search ............ 435/68.1, 91, 176, 172.1, 435/172.3, 320, 822, 320, 822, 252.3; 536/27; 935/6, 8, 9, 22, 24, 27, 29, 38, 41, 59, 60, 66, 72

[56] References Cited

PUBLICATIONS

Buzby et al., 1983 *J. Bacteriol* 154: 1446–1450.
Morrison et al. 1984 *J. Bacteriol* 159: 870–876.
Glass, Robert E. 1982 Gene Function Univ. Calif. Press Berkeley, pp. 364–365.
De Lorimier et al., 1984 *PNAS* 81: 7946–7950.
Mol. Gen. Genet. 199: 372–380, 1985. P. M. Andreoli. Versatile *Escherichia Coli–Bacillus* Shuttle Vectors Derived from Runaway Replication Plasmids Related to CloDF13.
Science 230: 805–807, 1985. J. S. Buzby et al., Expression of the *Escherichia Coli lac Z* Gene on a Plasmid Vector in a Cyanobacterium.
Gene 34: 363–366, 1985. M. Heusterpreute et al., Vectors with Restriction–Site Bands. III. *Escherichia Coli–Saccharomyces Cerevisiae* Shuttle Vectors.
Gene 39: 281–286, 1985. K. Miwa et al. Construction of Novel Shuttle Vectors and a Cosmid Vector for the Glutamic Acid–Producing Bacteria *Brevibacterium lactofermentum* and *Corynebacterium glutamicum*.
Appl. Environ. Microbiol. 50: 540–542, 1985., J. van der Vossan et al. Construction of Cloning, Promoter–Screening, and Terminator–Screening Shuttle Vectors for *Bacillus Subtilis* and *Streptococcus Lactis*.
Gene 30: 69–77, 1984. C. Morandi et al. Expression of Human Dihydrofolate Reductase cDNA and Its Induction by Chloramphenicol in *Bacillus Subtilis*.
Biotechnology 3: 69–72, 1985. L. Meile et al. Potential Shuttle Vectors Based on the Methanogen Plasmid pMEZ001.

*Primary Examiner*—Thomas G. Wiseman
*Assistant Examiner*—Richard C. Peet
*Attorney, Agent, or Firm*—Scully, Scott, Murphy & Presser

[57] ABSTRACT

This invention provides a biphasic shuttle vector capable replication and expression of foreign genetic information in *Escherichia coli* and *Agmenellum quadruplicatum* comprising an *E. coli* replicon, an *A. quadruplicatum* replicon, at least two selectable markers and a promoter derived from *A. quadruplicatum*. The invention further provides an ectopic mutant of *Agmenellum quadruplicatum* PR-6 characterized by displaying less AquI interference with unmodified plasmids than the PR-6 strain.

9 Claims, 5 Drawing Sheets

TRANSLATION OF -cpclacI. sequence

```
382   ATG TTT GAT ATT TTT ACC CGG GGA TCC GTC GAC CTG CAG CCA AGC   426
      MET Phe Asp Ile Phe Thr Arg Gly Ser Val Asp Leu Gln Pro Ser

427   TTG GCA CTG GCC CTG GCC GTC GTT TTA CAA CGT CGT GAC TGG GAA   471
      Leu Ala Leu Ala Leu Ala Val Val Leu Gln Arg Arg Asp Trp Glu

472   AAC CCT GGC GTT ACC CAA CTT AAT CGC CTT GCA GCA CAT CCC CCT   516
      Asn Pro Gly Val Thr Gln Leu Asn Arg Leu Ala Ala His Pro Pro
```

MOLECULAR WEIGHT = 5014.499 DALTONS

TRANSLATION OF- LacIZY. sequence

```
1287  ATG ACC ATG ATT ACG GAT TCA CTG GCC GTC GTT TTA CAA CGT CGT   1331
      MET Thr MET Ile Thr Asp Ser Leu Ala Val Val Leu Gln Arg Arg

1332  GAC TGG GAA AAC CCT GGC GTT ACC CAA CTT AAT CGC CTT GCA GCA   1376
      Asp Trp Glu Asn Pro Gly Val Thr Gln Leu Asn Arg Leu Ala Ala

1377  CAT CCC CCT TTC GCC AGC TGG CGT AAT AGC GAA GAG GCC CGC ACC   1421
      His Pro Pro Phe Ala Ser Trp Arg Asn Ser Glu Glu Ala Arg Thr

1421
```

MOLECULAR WEIGHT = 5166.541 DALTONS

FIG. 4 pAQE19LPC
14.3 kb

BIPHASIC SHUTTLE VECTORS

FIELD OF THE INVENTION

This invention relates to the field of genetic engineering. More specifically the invention relates to hybrid plasmids useful as shuttle vectors permitting the cloning and expression of foreign genetic information in at least two different species of host organism.

BACKGROUND OF THE INVENTION

Plasmids are extrachromosomal genetic elements and are capable of autonomous replication within their hosts. Bacterial plasmids range in size from 1 Kb to 200 Kb or more and encode a variety of useful properties. Plasmid encoded traits include resistance to antibiotics, production of antibiotics, degradation of complex organic molecules, production of bacteriocins, such as colicins, production of enterotoxins, and production of DNA restriction and modification enzymes. Although plasmids have been studied for a number of years in their own right, particularly in terms of their replication, transmissibility, structure and evolution, with the advent of genetic engineering technology the focus of plasmid research has turned to the use of plasmids as vectors for the cloning and expression of foreign genetic information. In its application as a vector, the plasmid should possess one or more of the following properties. The plasmid DNA should be relatively small but capable of having relatively large amounts of foreign DNA incorporated into it. The size of the DNA insert is of concern in vectors based on bacteriophages where packing the nucleic acid into the phage particles can determine an upper limit. The plasmid should be under relaxed replication control. That is, where the replication of the plasmid molecule is not strictly coupled to the replication of the host DNA (stringent control), thereby resulting in multiple copies of plasmid DNA per host cell. The plasmid should express one or more selectable markers, such as the drug resistance markers, mentioned above, to permit the identification of host cells which contain the plasmid and also to provide a positive selection pressure for the maintenance of the plasmid in the host cell. Finally the plasmid should contain a single restriction site for one or more endonucleases in a region of plasmid which is not essential for plasmid replication. It is particularly useful if such a site is located within one of the drug resistance genes thereby permitting the monitoring of successful integration of the foreign DNA segment by insertional inactivation. For example, when a plasmid contains two drug resistance genes and one of the genes contains a single restriction endonuclease site, the foreign DNA when ligated into that site will interrupt the expression of the drug resistance gene, thus converting the phenotype of the host from double drug resistance to single drug resistance. A vector as described above is useful for cloning genetic information, by which is meant integrating a segment of foreign DNA into the vector and reproducing identical copies of that information by virtue of the replication of the plasmid DNA.

The next step in the evolution of vector technology was the construction of so-called expression vectors. These vectors are characterized by their ability not only to replicate the inserted foreign genetic information but also to promote the transcription of the genetic information into mRNA and its subsequent translation into protein. This expression requires a variety of regulatory genetic sequences including but not necessarily limited to promoters, operators, transcription terminators, ribosomal binding sites and protein synthesis initiation and termination codons. These expression elements can be provided with the foreign DNA segment as parts thereof or can be integrated within the vector in a region adjacent to a restriction site so that when a foreign DNA segment is introduced into the vector it falls under the control of those elements to which it is now chemically joined.

In a more recent development, hybrid vectors have been constructed which permit the cloning and/or expression of foreign genetic information in more than one host. These biphasic or shuttle vectors are characterized as having separate origins of replication (replicons) to permit replication of the plasmid in the desired host; further, in the case of expression vectors, it may be required to have two sets of regulatory elements, each specific for the intended host. Such duplication of regulatory elements is not always required as it may be possible for a single promoter to be able to function in both of the desired hosts. Regardless of the type of biphasic vector, be it either a cloning or expression vector, it is preferred to have at least two selectable markers, one permitting selection in each of the contemplated hosts.

Examples of biphasic vectors include: a bifunctional plasmid (pMP358) capable of cloning and expressing human dihydrofolate reductase cDNA in both *Escherichia coli* and *B. subtilis* (Morandi, C et al. (1984) *Gene* 30:69-77) and a multifunctional plasmid (pME2001) derived from a methanogen capable of replication in a variety of microbial host species (Meile, L. et al., (1985) *Bio/Technology* 3(1):69-72). Chimeric plasmid vectors, such as pHY460 and pHY310, were constructed from the streptococcal tetracycline resistance (Tc$^R$) plasmid pAM1 (9.2 kb) and the *E. coli* vector pACYC177 (3.7 kb). These bifunctional plasmids could replicate and express the Tc$^R$ gene in both *E. coli* and *B. subtilis*. Plasmids pHY460 (7.0 kb) and pHY310 (4.8 kb) contained the Tc$^R$ gene of pAM1 and the ampicillin resistance (Ap$^R$) gene of pACYC177. Both plasmids showed high transformation efficiency in both host cells. pHY460 was maintained stably in *B. subtilis*. The PvuI, PstI, BglI and BanI sites in the Ap$^R$ gene and the HpaI, BalI and EcoRV sites in the Tc$^R$ gene can be used for selection of recombinant plasmids by insertional inactivation. In addition, plasmids pHY460 has unique sites for SacII, BstEII, XbaI, AvaI and BamHI. (Ishiwa, H et al., 1984, *Gene* 32:129-134). Bifunctional vectors (pMH158 and pTO 158) were constructed carrying selective markers and replicons derived from *E. coli* and *S. cerevisiae* and containing 21 and 23 unique restriction sites respectively (Heuterspreute, M. et al., (1985), *Gene* 34:363-366). A vector containing both kanamycin and thiostrepton resistance factors and capable of shuttling between *E. coli* and *Actinomyces* has been developed (*Biotechnol. Japan Newsservice* 3(10:8 (1985)). Other examples include: *E. coli-Bacillus* shuttle vectors derived from runaway replication plasmids related to Clo DF13 (Andreoli, P. M., (1985) *Mol. Gen'l Genet.* 199(3):372-380); shuttle vectors suitable for selection of regulatory sequences in *B. subtilis* and *Streptococcus lactis* (Van der Vossen, J.M.B.M., (1985) *Appl. Environ. Microbiol.* 50(2):540-542); a chimeric plasmid capable of shuttling between at least two bacterial species including *E. coli, Bacillus* or *Cornynebacterium* (European Patent Application EP 0155594); a chimeric vector containing tetracycline and ampicillin resistance genes and replication origin derived from *E. coli* and *Streptomyces fecalis* (European Patent Application 0162725); a shuttle vector capable of transformation of *E. coli* and *Acetobactor aceti* (Fukaya, M. et al. (1985) *Agric. Biol. Chem.* 49(7):2083-2090); a shuttle vector capable transforming both *E. coli* and *Gluconobacter suboxydans* (Fukaya, M. et al. (1985) *Agri. Biol. Chem.* 49(8):2407-2411); a shuttle vector capable of functioning in both *Brevibacterium lactofermentum* and *Cornybacterium glutamicum* (Miwa, K. et al. (1985) *Gene* 39:281-286); chimeric plasmids capable of replicating in *E. coli* and *Saccharomyces cereviriae* (PCT Patent Appln. WO 85/05632) and shuttle vectors capable of transforming both *Zymomonas mobilis* and *E. coli* (Tonomura, K. et al., (1986) *Agric. Biol. Chem.* 50(3):805-808).

This invention provides shuttle vectors capable of replication and expression of foreign genetic information in a cyanobacterium and *E. coli*. More specifically this invention relates to the use of DNA sequences to construct biphasic shuttle vectors for use in the cyanobacterium *Agmenellum quadruplicatum* strain PR-6 (hereinafter called PR-6), also identified as Synechococcus sp. 7002 (deposited in the American Type Culture Collection as ATCC 27264) and the eubacterium *Escherichia coli*. This invention also deals with the use of these shuttle vectors to introduce foreign genes into said cyanobacterium, for example the β-galactosidase gene of *E. coli*. Various aspects of this invention have been disclosed by the inventors in an article in *Science* 230:805-807 (Nov. 15, 1985) the contents of which are incorporated herein by reference.

BRIEF DESCRIPTION OF THE INVENTION

This invention provides a biphasic shuttle vector capable of replication and expression of foreign genetic information in *Eschericia coli* and *Agmenellum quadruplicatum* comprising an *E. coli* replicon, an *A. quadruplicatum* replicon, at least two selectable markers and a promoter derived from *A. quadruplicatum*.

In a further embodiment this invention provides a nucleic acid promoter isolatable from *Agmenellum quadruplicatum* on an 850 bp Hind III - Sma I fragment of the c-phycocyanin genetic region and, when correctly combined a structural gene, capable of directing the expression of said gene in *E. coli* and *Agmenellum quadruplicatum*.

In a further embodiment this invention provides an ectopic mutant of *Agmenellum quadruplicatum* PR-6 characterized by displaying less AquI interference with unmodified plasmids than the PR-6 strain.

In a final embodiment this invention provides a method for recombinant gene expression in *E. coli* and *A. quadruplicatum* the improvement which comprises employing as an expression vector a biphasic shuttle vector capable replication and expression of foreign genetic information in *Eschericia coli* and *Agmenellum quadruplicatum* comprising an *E. coli* replicon, an *A. quadruplicatum* replicon, at least two selectable markers and a promoter derived from *A. quadruplicatum*.

DETAILED DESCRIPTION OF THE FIGURES

FIG. 4 illustrates the translational fusion product between the c-phycocyanin gene and the β-galactosidase gene.

DETAILED DESCRIPTION OF THE INVENTION

The cyanobacteria are the simplest organisms that make use of both photosystems I and II and assimilate inorganic nitrogen in a manner similar to that of higher plants. Their prokaryotic organization makes them a potentially ideal model system in which to study these complex processes at the molecular level. *Agmenellum quadruplicatum* PR-6 (Synechococcus sp., PCC7002 and ATCC2764) has an efficient, well-characterized, natural DNA uptake system and can grow as a facultative photoheterotroph in the presence of glycerol. Several of the genes encoding components of the light collection apparatus have been isolated and characterized. Hence, PR-6 is well suited for genetic analysis of the photosynthetic mechanism with plasmid-generated merodiploids. An important aspect of this analysis involves the expression of these PR-6 genes under controlled conditions in which their promoters are fused to the easily assayable *Escherichia coli* β-galactosidase gene.

Transformation of PR-6 with biphasic plasmids has been described (Buzby, J. S. et al., (1983) *J. Bacteriol.* 154:1446). The main obstacle to the general use of bipnasic plasmids as cloning vehicles has been the endogenous PR-6 restriction system, Aqu I, an isoschizomer of Ava I. Since the presence of these restriction sites and the larger monomeric plasmid size have adverse effects on plasmid transformation efficiency in PR-6 derivatives of these original vectors were constructed with a view to overcoming the above adverse effects.

Figure 1:
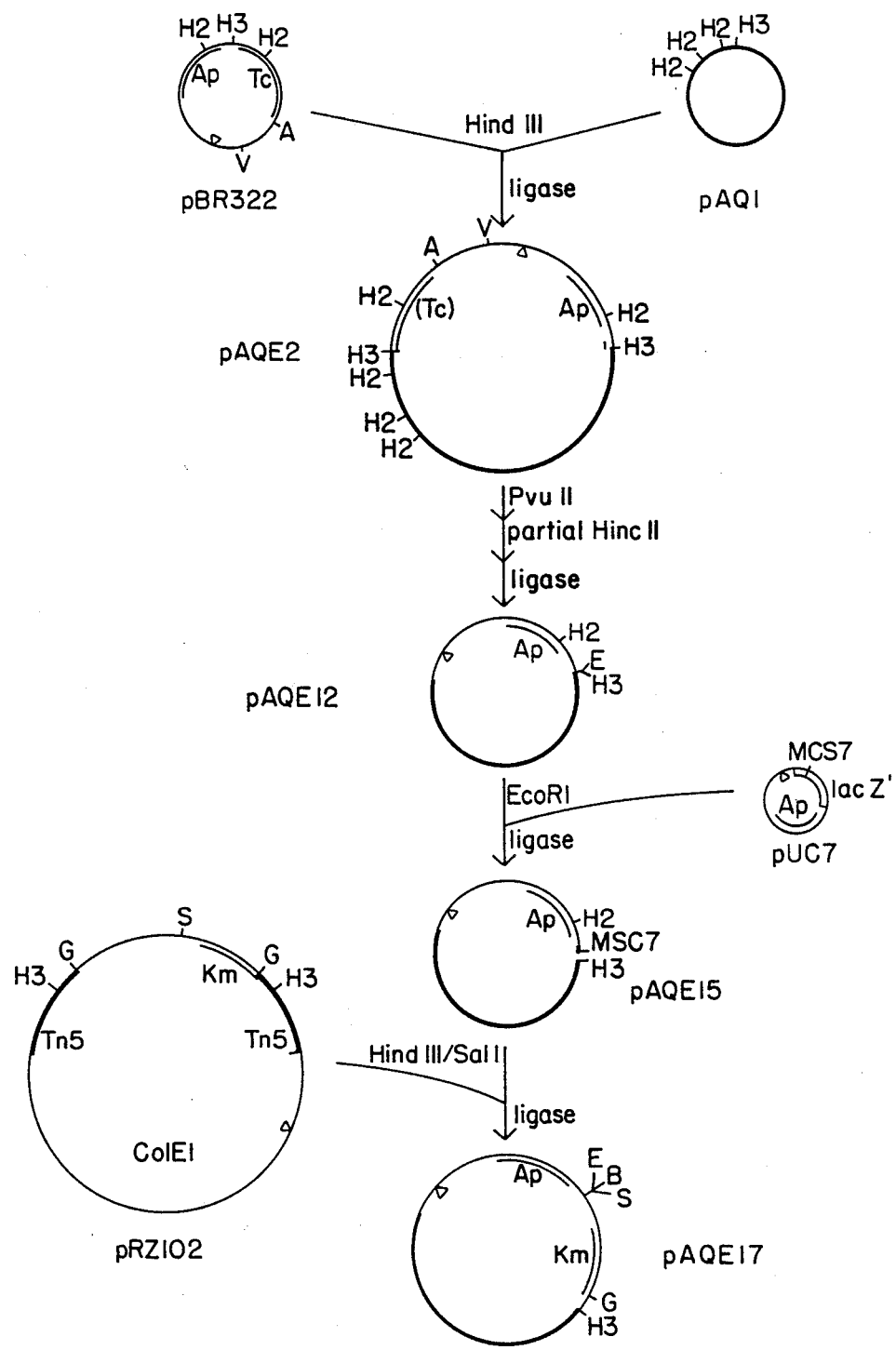
FIG. 1 illustrates the development of biphasic plasmid shuttle vectors for use in PR-6. The details of construction and a key to the abbreviations may be found in the "Detailed Description of the Invention".

The development of biphasic plasmid shuttle vectors useful for practicing this invention is illustrated in FIG. 1. With reference to FIG. 1, the smallest cryptic PR-6 plasmid, termed pAQ1 (Buzby, et al. supra) 4.6 kilobase pairs, was purified and joined with pBR322 (Bolivar, F. et al., (1977) *Gene* 2:95) at their unique Hind III sites in the construction of the first series of biphasic plasmids, represented by pAQE2 (8.9 kb). These plasmids were Tc$^s$ (tetracycline-sensitive) and Ap$^r$ (Ampicillin resistant). The Ava I restriction site, sequences of the nonfunctional Tc$^r$ gene, and about 1.0 kb of pAQ1 DNA were eliminated by Pvu II-partial Hinc II digestion and religation to create pAQE12 (5.9 kb). Cloning the 50-base pair restriction site polylinker from pUC7 (Vieira, J. et al., (1982) *Gene* 19:259), MCS7, into the Eco RI site on pAQE12 effectively provided the new vector pAQE15 (5.9 kb) with at least five unique, available cloning sites (Hind III, Eco RI, Bam HI, Sal I, and Acc I). The NPT II gene, encoding Km$^r$ and NM$^r$ was cloned from pRZ102 (Rothstein, S. J. et al., (1981) *Cell* 23:191) into pAQE15 as diagramed. The resulting plasmid, pAQE17 (7.3 kb), had at least eight unique, available cloning sites: Hind III, Eco RI, Bam HI, Sal I, Acc I, Ava I, Sma I, and Bgl II. The lysis by alkali procedure (Maniatis, T. et al., (1982) "Molecular Cloning: A Laboratory Manual", Cold Spring Harbor Laboratory) was used for plasmid isolations from both *E. coli* and PR-6. Restriction sites: H3, Hind III; H2, Hinc II; A, Ava I or Aqu I; B, Bam HI; E, Eco RI; S, Sal I; G, Bgl II; V, Pvu II; and P, Pst I. Heavier lines indicate pAQ1 sequences, and small triangles show ColE1 replication origins.

With the construction of pAQE12 and the transformation protocol outlined in Table 1, an average of $4.6 \times 10^4$ transformants per microgram of DNA are obtained, whereas $1.3 \times 10^5$ transformants were obtained for the dimer, pAQE13. The neomycinphosphotransferase (NPT) II gene from Tn5 was cloned into pAQE15 to give pAQE17 as described above. pAQE17 transformants of PR-6 can be selected at neomycin or kanamycin concentrations of 10 to 1000, $\mu g/ml$. With pAQE17, selection for kanamycin resistance ($Km^r$) gives about a fivefold higher level of PR-6 transformants than does $Ap^r$ selection and also gives more consistent and reproducible results from experiment to experiment. pAQE17 yields $1.3 \times 10^5$ transformants per microgram with $Km^r$ selection, whereas its dimer, pAQE18, yields $3.2 \times 10^5$ transformants per microgram.

Figure 2:
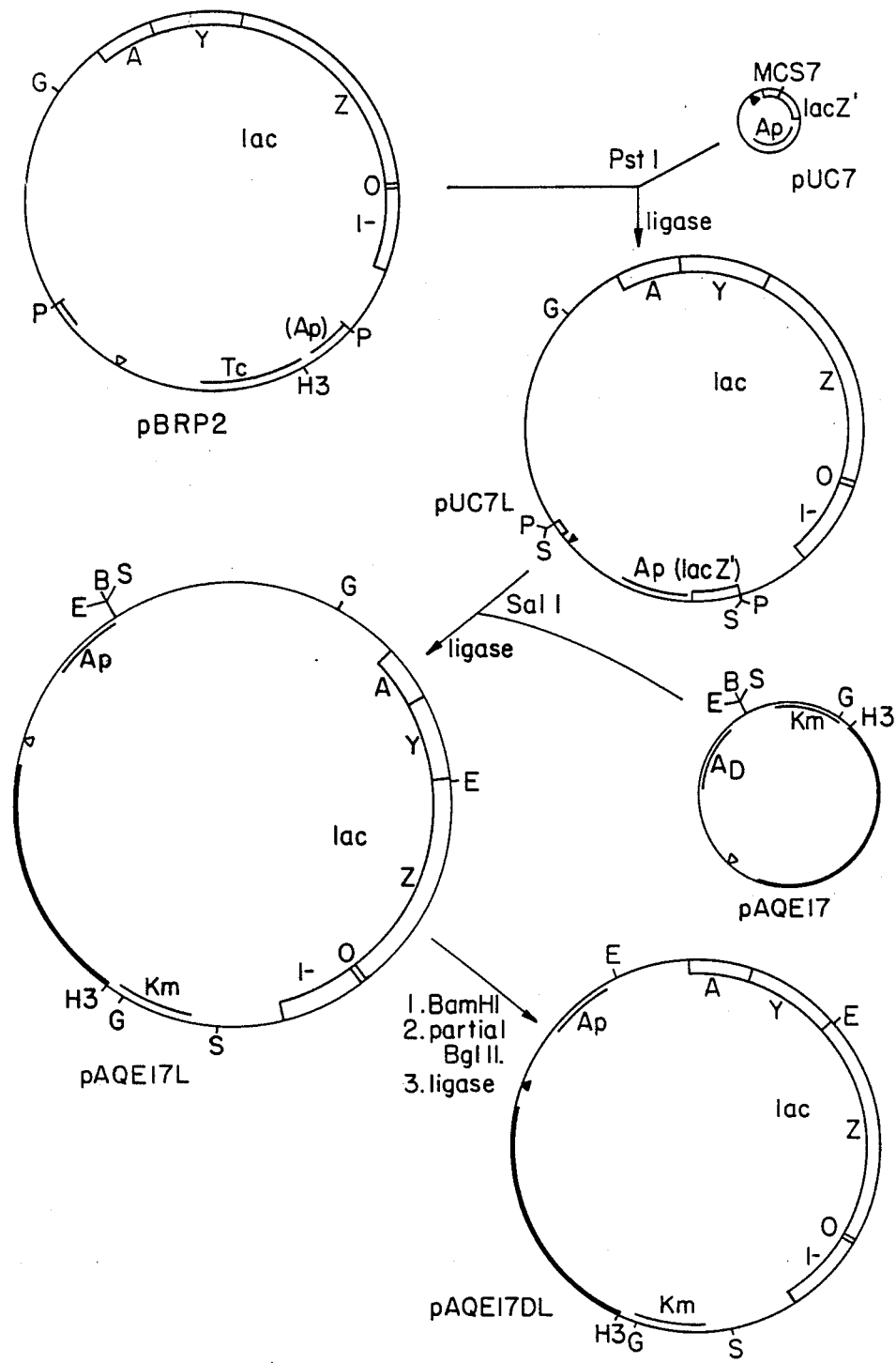
FIG. 2 illustrates the strategy for the cloning of the *E. coli* lac operon into a PR-6 shuttle vector. Details of the construction may be found in the "Detailed Description of the Invention".

The strategy for cloning the lac operon into pAQE17 is outlined in FIG. 2. With reference to FIG. 2, the initial Pst I-lac clone in pBR322, pBRP2, (15.3 kb), was identical to pBRP1 except that it has been converted to lacI$^-$ by homogenization in a lacI3 strain of *E. coli* (KL695). The Pst I-lac fragment from pBRP2 was cloned into the Pst I site in pUC7 so that lac can be obtained as a SalI fragment making possible the use of a unique cloning site on pAQE17. After the lac operon was cloned into the pAQE17 Sal I site, the resulting plasmid (pAQE17L; 18.3 kb) was subjected to Bam HI-partial Bgl II digestion (followed by religation) to remove about 3 kb of excess, nonessential DNA and reduce the plasmid's size, thereby increasing its potential transformation efficiency. The new plasmid pAQE17DL (15.3 kb), was prepared in the recombination-proficient (lac) *E. coli* strain, RDP244, to obtain a multimeric mixture, further enhancing its potential transformation efficiency.

The final vector construct pAQE17DL, still contained four Aqu I recognition sites in the lac fragment and one in pAQE17 itself. When pAQE17DL was used to transform wild-type PR-6, transformants resistant to both kanamycin and ampicillin could be detected, but they had all deleted most of the lac fragment and undergone significant recombinational rearrangements, as had pAQE7 (a derivative of pAQE2 carrying the NPT I gene and six Ava I sites).

Elimination of Aqu I restriction activity in the cells represented one method for circumventing degradation of susceptible plasmids during transformation. It had already observed that mutagenesis by way of ectopic integration during transformation is a highly effective method for generating random PR-6 mutants, as judged by observation of recombinants with altered pigmentation and colony morphology. This phenomenon was identified in Pneumococcus and its mechanism has also been studied in that organism. The strategy employed here is a variation of the procedures reported for Pneumococcus. It involved ligating random fragments of total PR-6 DNA, generated by partial digestion with Sau 3A, to the TnI $Ap^r$ gene fragment obtained by digestion of pDS1106 (Dougan, G. et al., (1977) *Mol. Gen. Genet* 151:151) with Bam HI and Pvu II. This produced DNA molecules that were initially linear and incapable of either ready circularization or autonomous replication. It was hoped that integration of these $Ap^r$ molecules into the PR-6 genome in the region of their homology would cause either insertional or deletional inactivation of the Aqu I restriction endonuclease gene by any one of a number of possible mechanisms. Similar techniques have been employed for generating specific mutations in *Bacillus subtilis* (Ferrari, F. A. et al., (1983) *J. Bacteriol.* 154:1513) *Saccharomyces cerevisiae* (Shortle, D. et al., (1982) *Science* 217:371), and *Dictyostelium discoideum* (Barclay, S. L. et al., (1983) *Mol. Cell Biol.* 3:2117), as well as in Pneumococcus (Morrison, D. A. et al. (1984) *J. Bacteriol.* 159:870). Integration of a drug resistance gene inserted into the host genome in vitro has also been demonstrated in the closely related cyanobacterium *Anacystis nidulans* R2, although it was not used to produce mutations directly (Williams, J. G. K. et al., (1983) *Gene* 24:37).

Figure 3:
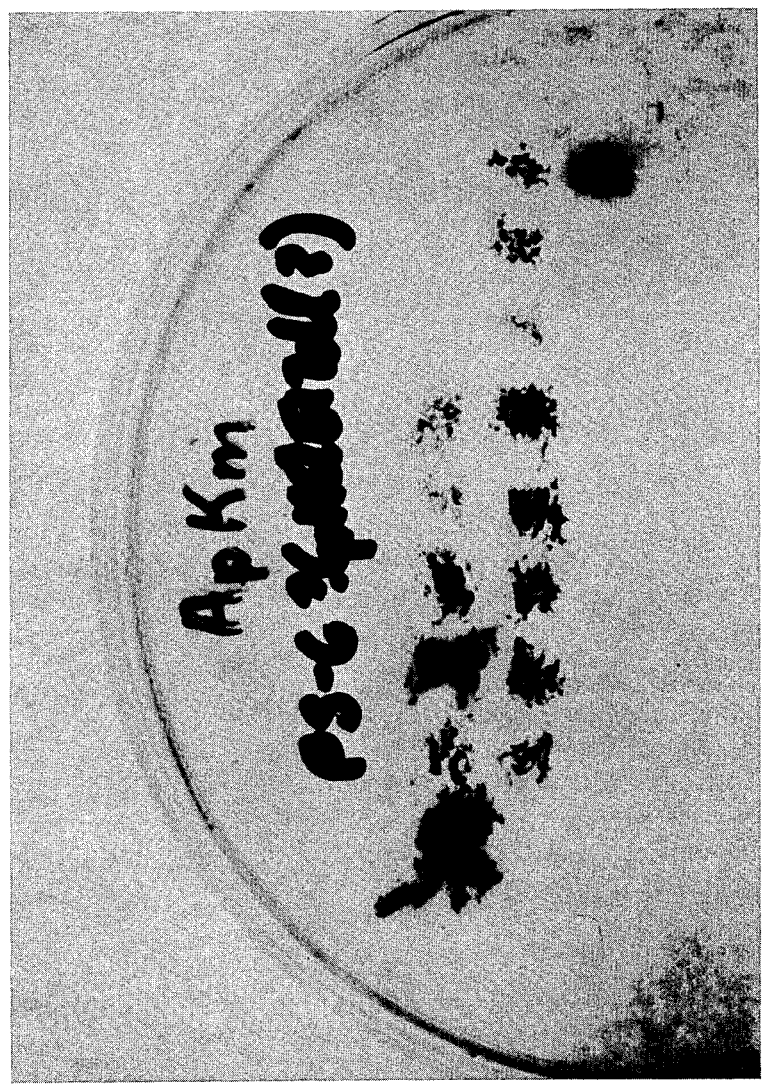
FIG. 3 illustrates the reaction of X-gal with patch of PR-6 containing pAQE17DL and evidences the production of β-galactosidase by the transformed strain.

A pool of $Ap^r$ recombinants selected in liquid culture (ampicillin, 10 ug/ml) after transformation of wild-type PR-6 with the above ligation mixture was subsequently transformed with Aqu I-sensitive pAQE17DL. Several hundred $Km^r$ transformants were obtained in this manner. Transformed colonies were overlayed with X-gal (5-bromo-4-chloro-3-indolyl- D-galactopyranoside) (Sigma) in 0.6 percent agar to 40 $\mu g/ml$, and the appearance of blue coloration was sought. Although difficult to discern against the dark green background, some colonies appeared to be slightly blue in color. This was confirmed by exposing replicas of the colonies to chloroform vapor for 30 minutes and then overlaying them with 0.6 percent agar containing lysozyme at a final concentration of 100 $\mu g/ml$ and either X-gal at a final concentration of 40 $\mu g/ml$ or o-nitrophenyl-D-galactopyranoside (ONPG) (Signma) at a final concentration of 120 $\mu g/ml$. An X-gal reaction with some patches of PR-6 containing pAQUE17DL is shown in FIG. 3. Both of these techniques produced a much more definitive coloration than did intact cells, with the blue color produced from X-gal being more persistent than the yellow from ONPG. Three of these transformants (G23, G25, and G38) actually expressed $\beta$-galactosidase activity with this procedure.

Six hundred of the $Km^r$ transformants from the same pool of random ectopic mutants were also tested by colony hybridization (Hanahan, D. et al., (1983) *Method of Enzymol.* 100B:333), with 12 showing hybridization to a $^{32}P$-labelled M13mp8 probe, which carries an 800-base pair fragment from the lac operon (Messing, J. et al., (1982) *Gene* 19:269). One of these (D52) was tested for $\beta$-galactosidase activity and found to elicit a positive response. Plasmid DNA, extracted from this transformant and from two of the Lac$^+$ transformants selected visually (G25 and G38), contained intact pAQE17DL after transformation back into *E. coli*. It is possible that some or all of these mutants are siblings, but they have been carried through further experimentation for comparison purposes.

The Lac$^+$ transformants were cured of pAQE17DL by streaking and gridding on nonselective A medium and replica plating for $Km^r$. The segregants obtained were retransformed to test for enhanced transformation efficiency of Aqu I-sensitive plasmids. A randomly selected $Ap^r$ ectopic recombinant, A0, was used as a control for these experiments, since the presence of the $Ap^r$ fragment in the PR-6 chromosome, homologous with the $Ap^r$ gene on the pBR322-derived vectors, approximately doubled overall transformation efficiency by itself. Kanamycin-sensitive segregants of G23 and G38 were transformed with a series of biphasic plasmids containing up to six Aqu I recognition sites, and their transformation efficiencies were compared to that of A0. The results are shown in Table 1.

TABLE 1

Relation of plasmid transformation efficiencies to their number of Ava I or Aqu I sites for PR-6 ectopic recombinants.

| Plasmid | Number of Aqu I sites | PR-6 strain | $KM^r$ transformants per $CFU^2$ |
|---|---|---|---|
| pAQE19 | 0 | A0 | $9.3 \times 10^{-4}$ |
| pAQE19 | 0 | G23 | $2.0 \times 10^{-3}$ |
| pAQE19 | 0 | G38 | $9.9 \times 10^{-4}$ |
| pAQE17 | 1 | A0 | $9.2 \times 10^{-4}$ |
| pAQE17 | 1 | G23 | $1.1 \times 10^{-3}$ |
| pAQE17 | 1 | G38 | $7.6 \times 10^{-4}$ |
| pAQE17L | 5 | A0 | $1.2 \times 10^{-5}$ |
| pAQE17L | 5 | G23 | $5.4 \times 10^{-5}$ |
| pAQE17L | 5 | G38 | $4.1 \times 10^{-5}$ |
| pAQE7 | 6 | A0 | $<2.9 \times 10^{-8}$ |
| pAQE7 | 6 | G23 | $2.6 \times 10^{-6}$ |
| pAQE7 | 6 | G38 | $1.1 \times 10^{-6}$ |

[2]CFU, Colony-forming unit

The above data were obtained by a plasmid transformation protocol that is a slight variation of the procedure described earlier (Buzby, et al., (1983) supra). A PR-6 liquid culture was grown to 20±1 percent transmittance (about $4 \times 10^7$ cells per milliliter; late log phase), measured at 550 nm, in medium A (Stevens, S. E. Jr., et al., (1973) J. Phycol. 9:427). A 0.1 volume of plasmid DNA was added to 0.9 volume of competent cells (at least 1 to 2 μg/ml for maximum levels). This transformation mixture was incubated for 60 to 90 minutes at 39° C. with light and $CO_2$. Dilutions in medium A were plated on the surface of medium A agar plates with 2.5 ml of 0.8 percent agar used per plate. Expression for 40 to 48 hours was carried out at 30°±2° C. with reduced illumination (plates were covered with a single sheet of typing paper). Platings were challenged with Ap (2 μg/ml) or Km (200 μg/ml) by overlaying them with 2 ml of 0.6 percent agar containing the antibiotic. Transformed colonies appeared after about 4 days of incubation (no paper covering).

Both mutants were transformed about five times as frequently with pAQE17L (FIG. 2), as was A0. Using the permeabilization method described above, β-galactosidase activity was detected in 50 percent of the G23 transformants, 73 percent of the G38 transformants, and none of the A0 transformants. Likewise, G38 and G23 were transformed at least 40 times as frequently with the pAQE7 construct, as was A0, and 90 percent of these transformants contained the intact plasmid.

β-Galactosidase activity in the PR-6 mutants transformed with pAQE17DL was determined by use of whole cell extract assay developed for E. coli (Birge, E. A. et al., (1974) J. Mol. Biol. 83:447) One enzyme unit equals the amount of enzyme that hydrolyzes 1 nmol of ONPG in 1 minute at 28° C. For this assay, PR-6 was grown in liquid culture to the same density as for transformations in the presence of kanamycin (40 μg/ml). The absorbance of the hydrolyzed ONPG in the PR-6 samples was determined at 420 nm. An identically treated control stain without pAQE17DL, grown to the same density, was used as a blank, since chlorophyll a has a significant absorbance band at this wavelength. In both G23 G38, pAQE17DL produced $5.0 \times 10^{-7}$ enzyme units per colony-forming units. The same plasmid produced $8.4 \times 10^{-7}$ enzyme units per colony-forming unit in E. coli KL791. The plasmid used carries a lacI3 mutation, and lac inducibility or possible catabolite repression effects in PR-6 have not been specifically determined. These ectopic mutants of PR-6 greatly increase the ability to introduce cloned genes into the cyanobacterium by biphasic plasmid transformation.

Another approach was used to overcome the adverse affect of the presence of Aqu I sites on plasmids prepared from E. coli cells. This approach involved making a derivative of pAQE17, pAQE19, by removing the single remaining Aqu I site.

The biphasic shuttle vectors can also be used to introduce other foreign genes into E. coli or PR-6. For example, the gene that codes for the enzyme chymosin or the genes for the Bacillus thuringiensis endotoxin may be moved into PR-6 or between PR-6 and E. coli. At present, the gene for E. coli β-galactosidase serves as a readily recognized example or functional equivalent of other foreign genes.

Figure 5:
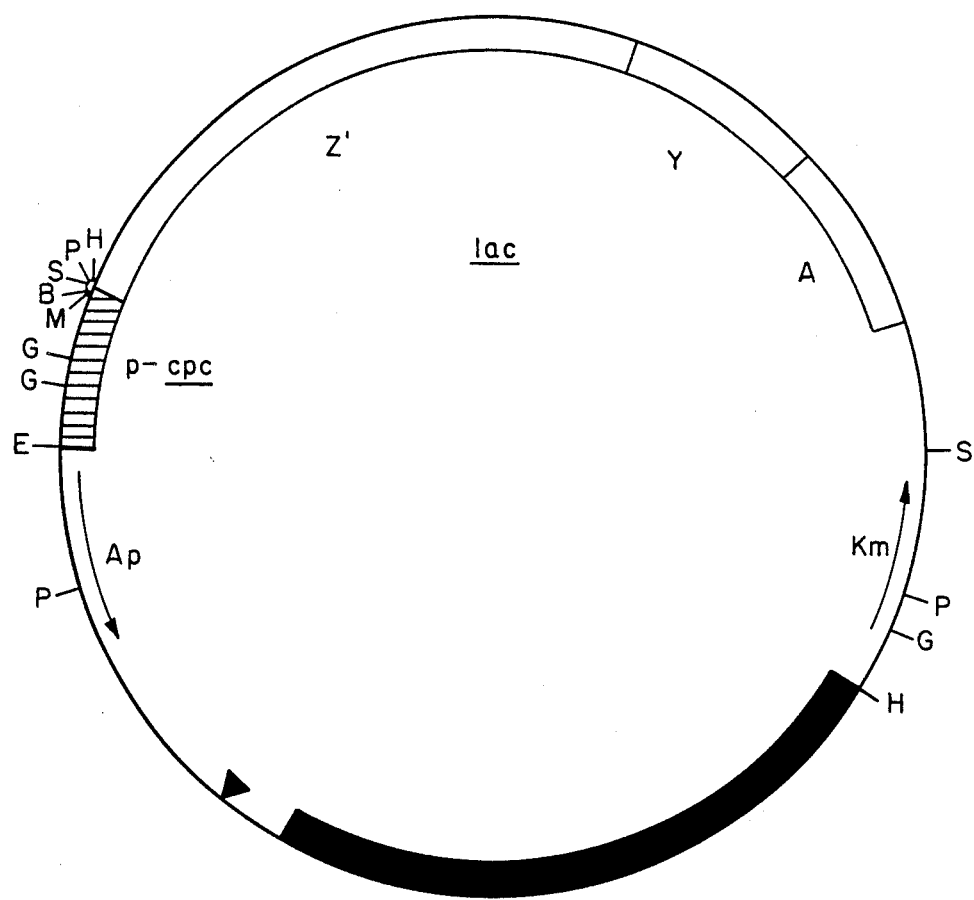
FIG. 5 illustrates a plasmid map of the pAQE19LPC biphasic shuttle vector. The abbreviations are those found in the description of FIG. 1.

To further illustrate the capacity of the vectors to express genetic information from a variety of sources, a translational fusion between the apoprotein subunit gene of c-phycocyanin from PR-6 and the lacZ gene from E. coli was constructed. An 850 bp HindIII-SmaI fragment from pAQPR1 (a pBR325 derivative with the c-phycocyanin region on a 3.1 kb HindIII fragment) was cloned into the SmaI site of the lac fusion vector pSKS107. This 850 bp fragment contains the phycocyanin apoprotein promoter and the beginning of the subunit gene. The fusion protein produced contains the first seven amino acids from the β subunit gene, ten amino acids from the linker region, and then the native β-galactosidase protein starting from amino acid number seven (FIG. 4). The E. coli β-galactosidase serves as a readily recognized example or prototype of foreign gene transfer into the cyanobacterium PR-6. This fusion was then moved to pAQE19 (a derivative of pAQE 17 described above) so that it could be transformed into either PR-6 or E. coli. This plasmid is called 'pAQE19LPC, and a map of the plasmid is shown in FIG. 5. A 550 bp BamHI - BglII fragment containing the phycocyanin promoter was removed from pAQE19LPC to yield a promoterless control plasmid, pAQE19LC.

β-galactosidase assays were run on exponentially growing cultures of E. coli strain KL791 (a lac deletion strain) containing pAQE17DL, pAQE19LPC, and pAQE19LC. Parallel β-galactosidase assays were run on exponentially growing cells of G38 (an ectopic mutant of PR-6) containing the same three plasmids. The results of these experiments are shown in Table 2.

TABLE 2

β-galactoside expression in A. quadruplicatum strain PR-6 and E. coli.

| | EU/cfu | |
|---|---|---|
| Plasmid | E. coli | PR-6 (G38) |
| pAQE19LC | $4.6 \times 10^{-9}$ | not detected |
| pAQE17DL | $3.1 \times 10^{-7}$ | $2.5 \times 10^{-7}$ |
| pAQE19LPC | $4.6 \times 10^{-6}$ | $1.4 \times 10^{-4}$ | pAQE17DL contains an intact E. coli lac operon with the lacI3 allele present to eliminate lac repressor synthesis. pAQUE19LPC contains a translational fusion of the beta c-phycocyanin gene from PR-6 and the lacZ gene from E. coli. pAQE19LC is a derivative of pA- QE19PLC where the PR-6 cpc promoter has been removed.

Samples were taken from exponentially growing cultures of E. coli strain KL791 or the G38 ectopic mutant of PR-6 containing the indicated plasmids for β-galactosidase assays. The E. coli cultures were at about $4 \times 10^7$ cfu/ml. Both organisms were at about $3 \times 10^8$ cfu/ml while the G38 cultures were treated with lysozyme and Brij-58 before ONPG was added. The reactions were run at 28C and were stopped by the addition of urea-carbonate. The samples were read at 420nm (G38 cells treated in parallel were used as a blank for the PR-6 samples) and enzyme units (EU) of β-galactosidase were calculated. One EU equals the amount of enzyme that hydrolyzes one nanomole of ONPG in one minute at 28C. On the basis of β-galactosidase activity per colony forming unit, the lac promoter from E. coli appears to function almost as well in the PR-6 strain as it does in E. coli. It should be noted that the lac region in pAQE17DL contains the lacI3 allele so that no functional repressor protein is made. Extremely high levels of β-galactoside were produced from the c-phycocyanin promoter in PR-6. The lack of detectable enzyme activity from pAQE19LC in PR-6 shows that it is, in fact, the cpc promoter that is responsible for β-galactosidase expression. It is also worthy of note the unexpected result that there is tenfold higher expression from the cpc promoter than the lac promoter in E. coli.

The strain useful in practicing the subject invention was deposited with the American Type Collection, 12301 Parklawn Drive, Rockville, Md. 20852, where after viability testing the following ATCC number was assigned:

| Strain | ATCC No. |
|---|---|
| Agmenellum quadruplication PR-6 (Synechococcus sp. 7002) | 27264 |
| Agmellum quadruplication G-38 | 53937 |
| Eschenchia coli KL791 PAQE19LPC | 68084 |

What is claimed is:

1. In a method for recombinant gene expression in E. coli and A. quadruplicatum, wherein a vector is employed to control gene expression the improvement which comprises employing as said vector a biphasic shuttle vector capable of replication and expression of a heterologous gene in E. coli and A. quadruplicatum, said vector comprising an E. coli replication origin and an A. quadruplicatum replication origin, at least two selectable markers and an A. quadruplicatum c-phycocyanin apoprotein promoter operably linked to said heterologous gene.

2. A biphasic shuttle vector capable of replication and expression of a heterologous gene in Escherichia coli and Agmenellum quadruplicatum comprising an E. coli replication origin, an A. quadruplicatum replication origin, at least two selectable markers and an A. quadruplicatum c-phycocyanin promoter operably linked to said heterologous gene.

3. The vector according to claim 2 having the characteristics of pAQE19LPC.

4. A biphasic shuttle vector capable of replication in E. coli and A. quadruplicatum having the essential characteristics of at least one of the vectors selected from the group consisting of pAQE12, pAQE13, pAQE13, pAQE15, pAQE17, pAQE18, pAQE19, and pAQE19LPC.

5. An Eschericia coli host transformed by the vector of claim 2 or 4.

6. An Agmenellum quadruplicatum host transformed by the vector of claim 2 or 4.

7. An ectopic mutant of Agmenellum quadruplicatum PR-6 characterized by displaying less AquI interference with unmodified plasmids than the PR-6 strain.

8. The ectopic mutant of claim 7 selected from the group D52, G23, G25 and G38.

9. An isolated DNA of A. quadruplicatum comprising an 850 bp HindIII-SmaI fragment encoding the promoter of the c-phycocyanin apoprotein gene operably linked to an heterologous gene and capable of directing expression of said gene in E. coli and A. quadruplicatum.

* * * * *

UNITED STATES PATENT AND TRADEMARK OFFICE
CERTIFICATE OF CORRECTION

PATENT NO. : 4,956,280

DATED : September 11, 1990

INVENTOR(S) : Jeffrey S. Buzby, et al.

It is certified that error appears in the above-identified patent and that said Letters Patent is hereby corrected as shown below:

Column 3, line 39: "Eschericia" should read as --Escherichia--

Column 3, line 59: "Eschericia" should read as --Escherichia--

Column 3, line 64: insert the following as a new paragraph --The file of this patent contains at least one drawing executed in color. Copies of this patent with color drawing(s) will be provided by the Patent and Trademark Office upon request and payment of necessary fee.--

Column 6, line 26: "-indolyo- D" should read as -- -indolyo-$\beta$ D--

Column 6, line 36: "(Signma)" should read as --(Sigma)--

Column 6, line 38: "pAQUE17DL" should read as --pAQUE 17DL--

Column 8, line 24: "the apoprotein" should read as --the $\beta$ apoprotein--

Column 8, line 66: "pAQUE19LPC" should read as --pAQE19LPC--

Column 9, line 31: "Type Collection" should read as --Type Culture Collection--

Column 9, line 37: "quadruplication" should read as --quadruplicatum--

Column 9, line 39: Agmellum quadruplication" should read as --Agmenellum quadruplicatum--

Column 9, line 40: "Eschenchia" should read as --Escherichia--

UNITED STATES PATENT AND TRADEMARK OFFICE
CERTIFICATE OF CORRECTION

PATENT NO. : 4,956,280

DATED : September 11, 1990

INVENTOR(S) : Jeffrey S. Buzby, et al.

It is certified that error appears in the above-identified patent and that said Letters Patent is hereby corrected as shown below:

```
        Column 10, line 25, Claim 4:  delete "pAQE13,"
        Column 10, line 36:  "group D52," should read
as --group consisting of D52,--
        Column 10, line 40:  "an" should read as --a--
```

Signed and Sealed this

Twenty-first Day of April, 1992

*Attest:*

HARRY F. MANBECK, JR.

*Attesting Officer*          *Commissioner of Patents and Trademarks*